(12) United States Patent
Battagliarin et al.

(10) Patent No.: US 6,170,556 B1
(45) Date of Patent: Jan. 9, 2001

(54) EQUIPMENT AND PROCESS FOR THE PREPARATION OF ELECTRIC CONDUCTING COMPOSITE SAMPLES FOR THE DIRECT INSTRUMENTAL ANALYSIS OF POWDERS

(75) Inventors: Marino Battagliarin, Lido di Venezia; Emilio Sentimenti, Fontane di Villorba; Letizia Meregalli, Venice, all of (IT)

(73) Assignee: ENIRISORSE S.p.A., Rome (IT)

( * ) Notice: Under 35 U.S.C. 154(b), the term of this patent shall be extended for 0 days.

(21) Appl. No.: 09/120,339

(22) Filed: Jul. 22, 1998

(30) Foreign Application Priority Data

Aug. 7, 1997 (IT) .............................. MI97A1897

(51) Int. Cl.[7] ................................................. B22D 19/14
(52) U.S. Cl. .............................. 164/97; 164/332
(58) Field of Search .................. 164/97, 271, 332, 164/334

(56) References Cited

U.S. PATENT DOCUMENTS 5,983,973 * 11/1999 Cornie ..................................... 164/97

FOREIGN PATENT DOCUMENTS 1-122654 * 5/1989 (JP) ........................................ 164/97

54-9132 * 5/1989 (JP) ........................................ 164/97

* cited by examiner

Primary Examiner—Kuang Y. Lin
(74) Attorney, Agent, or Firm—Oblon, Spivak, McClelland, Maier & Neustadt, P.C.

(57) ABSTRACT

Equipment for the preparation of electric conducting composite samples by infiltration in a mold characterized in that it essentially comprises:

a pressurization/infiltration chamber having at least one opening to connect it by means of appropriate tubes with a vacuum line and a pressure line and devices for sealing both under vacuum and under pressure;

a sample-holder, inside said chamber, made of a material with a high thermal conductivity with one or more seats in each of which a mold is housed consisting of:
    a chemically inert and thermally stable tube made of a non-porous material;
    a plug, situated at one end of the tube, of a material which is different from the tube;
    a chemically inert and thermally stable spacer of non-porous material, situated inside the tube in contact with the plug;

a device for creating a vacuum in the chamber;
a device for pressurizing the chamber;
a device for the thermal treatment of the sample-holder.

15 Claims, 2 Drawing Sheets

EQUIPMENT AND PROCESS FOR THE PREPARATION OF ELECTRIC CONDUCTING COMPOSITE SAMPLES FOR THE DIRECT INSTRUMENTAL ANALYSIS OF POWDERS

BACKGROUND OF THE INVENTION

1. Field of the Invention

The present invention relates to equipment and the relative process for the preparation of electric conducting composite samples starting from powders, (this term also comprising lyophilized organic compounds), in the form of matrices or as a carrier by impregnation, adsorption or dispersion of liquids or by impregnation or adsorption of gases, which may or may not be insulating and of an organic or inorganic origin, to be subjected to instrumental chemical analysis with techniques for the direct analysis of solid conductors.

2. Description of Prior Art

Various advanced instrumental techniques and/of of consolidated use, such as, for example, AAS, GFAAS, ICP-OES, ICP-MS, LC-ICP-MS, voltammetry, etc. can be used for the chemical characterization of organic and inorganic materials and in particular for the quantitative determination of element traces: in all cases there is dissolution of the sample and dilution in water.

Some alternative anlaytical techniques, capable of reaching detecting limits (LoD) for many elements of less than 1 ppb, such as SIMS, SSMS, GDMS, allow direct analysis of the sample without preliminary chemical attack and subsequent dilution.

An application limit of the latter pair of techniques is due to the necessity for the material under examination to be a (semi)conductor. In the contrary case, the matrix must be manipulated so as to obtain a sample for analysis which is conducting; for this purpose it is possible:

- to mix it with ligand metals (Ti, Cu, Ga, Ag and Ta are those most commonly used) or with graphite,
- to couple it to a secondary cathode, exploiting the partial redeposition effects of the vaporized metal coming from the cathode on the insulating sample,
- to subject it to infiltration, according to the preparative procedure described in "An innovative sample preparation procedure for trace and ultratrace analysis on non-conducting powders by direct current glow discharge mass spectrometry", (Battagliarin M., Sentimenti E., Scattolin R.—Spectrochimica Acta, Vol. 50B, Nr. 1, pages 13–25, 1995).

The equipment described in the article cited above essentially consists of a high pressure container which houses a mould containing the powder and metal to be melted and compressed.

The process using this equipment essentially comprises the following steps:

- introduction of the powder to be analyzed into a tube in PTFE of the equipment;
- insertion of a rod of low-melting metal ligand into the tube;
- vapor and gas evacuation and subsequent heating to melt the ligand;
- pressurization for the infiltration of the powder;
- cooling and extraction of the sample for analysis.

As an alternative to the above methods, sources can be used with discharge in alternating radio-frequency current (rf GDMS); the results so far obtained however, even if promising, are only partial and cannot be transferred to a commercial level.

For minimum quantities of material however, the infiltration system as a supporting means of the material of the sample is extremely useful if not indispensable.

Both the introduction of a conducting ligand and resort to a secondary cathode have a series of drawbacks which limit the instrumental performances.

The main disadvantages relating to each preparative method are summarized below:

- it is essential to apply very high pressures, on an average not less than 10–15 tonn/cm$^2$, with considerable stress of the moulds and relative contamination of the sample on the part of the material forming the mould itself;
- it is necessary to eliminate these surface contaminations by means of a vigorous chemical attack and a prolonged sputter etching;
- it is necessary to carefully clean the mould to minimize any possible residual effects;
- the ligands which are most suitable for the purpose and commercially available at reasonable prices, except for gallium and graphite, do not easily reach the desired degree of purity;
- a significant dilution of the sample is introduced with a decrease in the LoD;
- it is particularly difficult to obtain a satisfactory homogenization of the mixture resulting in a deterioration in the repeatability of the measurements;
- it is necessary to find the correct weight ratio ligand/matrix to have good mechanical resistance of the sample;
- traces of water adsorbed on the powder granules can significantly lower the sputtering yield and slow down the vaporization rate.

For coupling with a secondary cathode:

- it is essential to pellet the material to be analyzed by pressing with suitable moulds;
- residual effects are easily generated in the material in the mould, which must be eliminated with suitable chemical attacks;
- with this geometry the sputtering yield and detecting limits are lower than those obtained from rods;
- the selection of the material forming the cathode, the dimensions of the central hole (focal spot) of the cathode/mask, the presputtering and discharge conditions are extremely critical; consequently the set-up of an analysis protocol is rather complex;
- it is extremely important to have a mask made of material with a very high purity;
- optimum operating parameters vary considerably from matrix to matrix.

For infiltration in PTFE mould:

- equipment is used which already exists (designed for the preparation of composite materials with a metallic matrix [MMCs], for mechanical components by infiltration with molten aluminum and its alloys) which is greatly overdimensioned and cannot be easily installed in a sample preparation area of group 100 (for example, glove box);
- the design does not allow efficient control of the process development and it is therefore necessary to excessively prolong the residence times of the charge in the chamber to obtain complete melting of the ligand before applying the necessary pressure for infiltration;

the material used for the mould (PTFE) is easily deformed and can tolerate only a few operating cycles; the main components must be frequently substituted;

the seal (O-ring in Viton) does not ensure perfect insulation between the pressurized environment and the base of the charge;

the molten ligand cannot be adequately confined once compressed; this results in poor reproducibility of the end-dimensions of the sample for analysis and a consumption of ligand of more than 25–30% with respect to the useful quantity;

the molten ligand may come into contact with the seal;

the degree of vacuum which can be reached is relatively low (1–10 mbars), as is also the rate at which the gases adsorbed on the matrix are removed.

SUMMARY OF THE INVENTION

We have found new equipment for infiltration in mould which enables most of the disadvantages arising from both the equipment and processes of the known art described above to be overcome, also minimizing the necessity of material for the preparation of the samples and of characterizing matrices available in an extremely reduced quantity.

The equipment and relative process of the present invention can be used for both the qualitative and quantitative determination of minor elements and traces in mass spectrometry with glow discharge in direct current (direct current Glow Discharge Mass Spectrometry, or dc GDMS) and also, without any particular adaptations, with other similar instrumental techniques (SIMS, SSMS, ICP-MS laser ablation, ICP-OES spark ablation, GD-OES).

The equipment for the preparation of electric conducting composite samples by infiltration in mould, of the present invention, is characterized in that it essentially comprises:

a pressurization/infiltration chamber having at least one opening to connect it by means of appropriate pipes with a vacuum line and a pressure line and devices for sealing both under vacuum and under pressure;

a sample-holder, inside said chamber, made of a material with a high thermal conductivity with one or more seats, preferably vertically positioned, in each of which a mould is housed consisting of:

a chemically inert and thermally stable tube made of a non-porous material;

a plug, situated at one end of the tube, at the lower end in the case of a vertical seat, of a material which is different from the tube, preferably of the same metal forming the main parts of the chemical analysis instrument of said samples;

a chemically inert and thermally stable spacer of non-porous material, situated inside the tube in contact with the plug;

means for creating a vacuum in the chamber;

means for pressurizing the chamber;

means for the thermal treatment of the sample-holder.

The material to be selected both for the tube and spacer is preferably plastic: PTFE is preferred.

The material of the tube plug is preferably tantalum which is also the metal of which the main parts of the analytical instrument of the samples is normally made.

The process for preparing the electric conducting composite samples, which is a further object of the present invention, starting from a powder previously prepared with the equipment described above, essentially comprises the following steps:

charging a tube with the powder to be analyzed, after inserting the plug and spacer, this operation being effected either before or after the mould has been placed inside the sample-holder;

introduction of a solid ligand into the tube in the area above the powder;

closing the infiltration chamber after positioning a sealing device;

evacuation from the chamber of the vapor and gases adsorbed on the powder grains bringing the chamber under vacuum, preferably to a pressure of less than $5.10^{-2}$ mbars, more preferably equal to or less than $3.10^{-2}$ mbars.;

heating the supporting base of the chamber and consequently both the sampleholder and the mould in order to melt the ligand;

pressurization of the chamber up to a pressure of at least 30 bars, preferably between 40 and 50 bars;

extraction of the mould from the sample-holder, followed or preceded by cooling until the ligand has solidified, removal of the tube plug and extraction from the mould of the composite sample with consequent removal of the spacer.

In the case of particular composite samples it may be necessary to prepare the powder with particular steps among which mainly:

reduction or oxidation reactions or any reaction which can produce compounds with more thermal stability;

lyophilization;

preconcentration.

The reduction or oxidation reactions help to eliminate potential spectral interferences by suitably modifying the stoichiometric value to remove elements or groups which create interference in mass analysis or to obtain compounds which are thermally more stable at the melting points of the ligands.

Lyophilization is necessary for components of an organic origin which are not infiltrable as such.

Preconcentration, on the other hand, is necessary for separating the compounds or elements to be analyzed from the liquid or gaseous substances, by infiltrating the carrier, possibly porous and/or suitable for being polverized, onto which the analite has been cemented/adsorbed.

The steps described above can be carried out not only in specific equipment but also in equipment of the type described above with the addition of suitable means for effecting these steps.

These devices in the modified equipment can be present contemporaneously with the sample-holder or they can be interchanged in relation to the sequencing of the operations.

Apart from a practical advantage, it is advisable to carry out these operations inside the equipment when there is the danger of introducing possible environmental contaminations during transfer to the equipment in the atmosphere or when there is a low quantity of sample to avoid dispersions.

These operations, obviously carried out before infiltration, can be effected for reduction or oxidation reactions or for preconcentrations before charging the ligand into the tube, whereas in the case of lyophilization before or after charging into the tube.

In these cases the equipment in question can be modified with the possibility of interchanging the essential parts to insert the necessary modules.

In particular in the case of reactions there may be a sample-holder-reactor, feeding line/s, flush and/or output, in the case of lyophilization, a sample-holder-lyophilizer and a line under vacuum, in the case of preconcentration inlet/out lines and optionally a preheating device.

BRIEF DESCRIPTION OF THE DRAWINGS

FIG. 1 schematically illustrates the whole apparatus, whereas FIG. 2 is a vertical sectional view of the pressurization/infiltration chamber.

Figure 1:
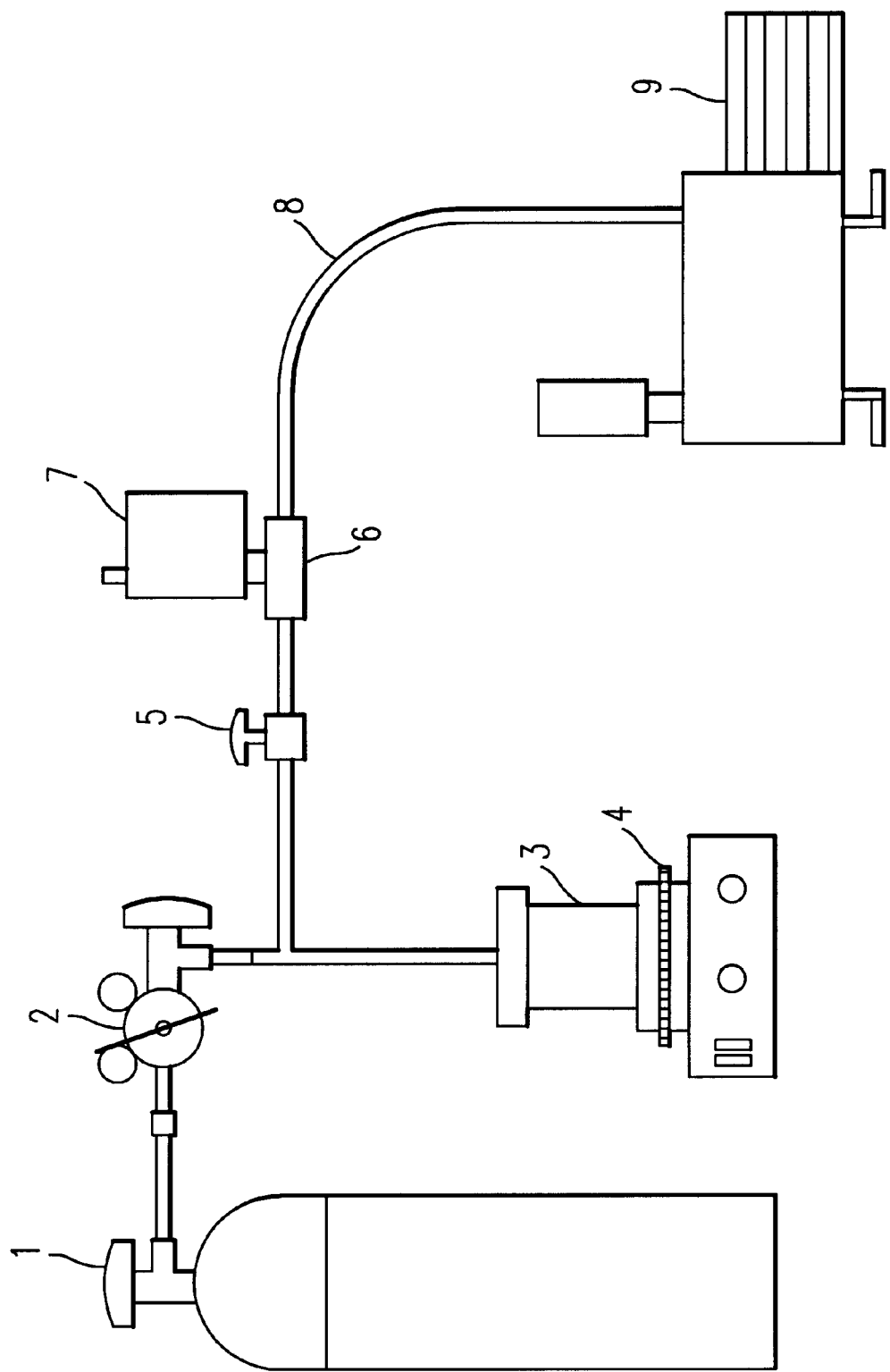
FIGS. 1 and 2 enclosed represent an embodiment of the equipment claimed, which however should not be considered as limiting the scope of the invention.

The equipment consists of:
- a pressurization/infiltration chamber with reduced dimensions (3) so as to allow preparation of the charge and assembly of the device in an environment protected from contamination (for example, glove box, glove bag) having a base (37) in contact with a heating element (4), a closing system (cover or head) (38), appropriate sealing devices (36) for the vacuum or pressure, an opening (39) for connection with the vacuum line or high pressure line;
- a vacuum line, in turn consisting of a two-step rotating pump (9), a reinforced PVC pipe (8), a vacuum measurer of the Pirani type (7): a manual. valve (5) separates the pressurization chamber from the pump at the moment of infiltration;
- an inert gas cylinder (1) connected to a two-step pressure reducer (2);
- a heating element (4);
- a cylindrically shaped sample-holder (33), with 12 seats for housing the same number of charges;
- tubes (31) and cylindrical spacers (32);
- plugs made of tantalum (30).

Inside the tubes (31) the powder charged and the ligand are marked with (34) and (35) respectively.

The use of the equipment claimed and relative preparation process of the electric conducting composite samples has the following advantages:
- the matrix under examination is confined in a well-defined region, with a drastic reduction in the dilution;
- as the analytical reference technique has a reduced consumption of material during trace analysis, the sample can be conserved to be subjected, after some time, to subsequent return analyses: possibility of integrating the initial information with further elements, without preparing other samples for analysis and at the same time verifying the reproducibility of the instrumental result;
- the signals characteristic of the types of components are stronger, with an improvement in the LoD;
- the homogeneity of the composite region subjected to erosive action of the plasma, is higher than that of a homologous sample prepared by cold pressing: this results in an improvement in the repeatability of the measurements;
- the necessity is reduced of material forming the sample for analysis: the test can be carried out on small quantities of matrix (a few milligrams) for prolonged times (several hours);
- thanks to the efficiency with which the matrix is confined, it is possible to analyze materials which are particularly precious and/or available in extremely reduced quantities (for example, microsamples from works of art, archeological findings, biological tissues);
- the analysis conditions of the composite are generally comparable to those used for massive conducting matrices;
- the mechanical stability of the samples for analysis exceeds that of homologous samples obtained by mixing and pressing at room temperature;
- the preferred ligands for this process are more easily available on the market with a high purity (5N and over) than powders, and at more advantageous prices with the same titer;
- the reduced dimensions of the equipment proposed allow the charge to be prepared and the infiltration chamber to be assembled under controlled conditions, in order to minimize environmental pollution;
- melting and infiltration are accelerated thanks to the reduction in the dimensions of the pressurization chamber and to the use of a metal with a high thermal conductivity for the construction of the chamber (3) and sample-holder (33);
- the improvement in the degree of vacuum during the melting of the ligand, in particular if coupled with treatment at a high temperature, contributes considerably to reducing the humidity, the main cause of the quenching of the plasma, and other adsorbed gases, the potential origin of spectral interferences;
- the parts made of PTFE (31), (32) are easily available, they do not require complex processing, they can be eliminated to prevent any residual effect;
- the molten ligand is effectively contained inside the tube (31) made of PTFE, in spite of the application at high pressures: samples for analysis are obtained with a reproducible length and non-contaminated by contact of the molten product with external parts;
- the spacer made of PTFE (32) eliminates any possible minor residual effects deriving from the direct contact between molten metal and sealing capsule made of Ta;
- thanks to the self-lubricating properties of the plastic material, the metal (35), although wetting the contact surface, is prevented from firmly sticking to it once it has solidified, creating problems of integrity of the sample at the moment of extraction;
- the seal (36) is situated in an area which is not in contact with the molten ligand.

Some examples are provided for a better illustration of the invention.

EXAMPLES

Both inorganic and organic materials were analyzed, which are electric conducting and insulating, in an attempt to maintain an average instrumental resolution to allow a significant comparison between the results of the various matrices. It is considered that a conventional masive matrix (Cu, Fe, Zn, etc.) produces an intensity signal on an average between 1.0 and 4.0 $10^{-10}$ A.

Figure 2:
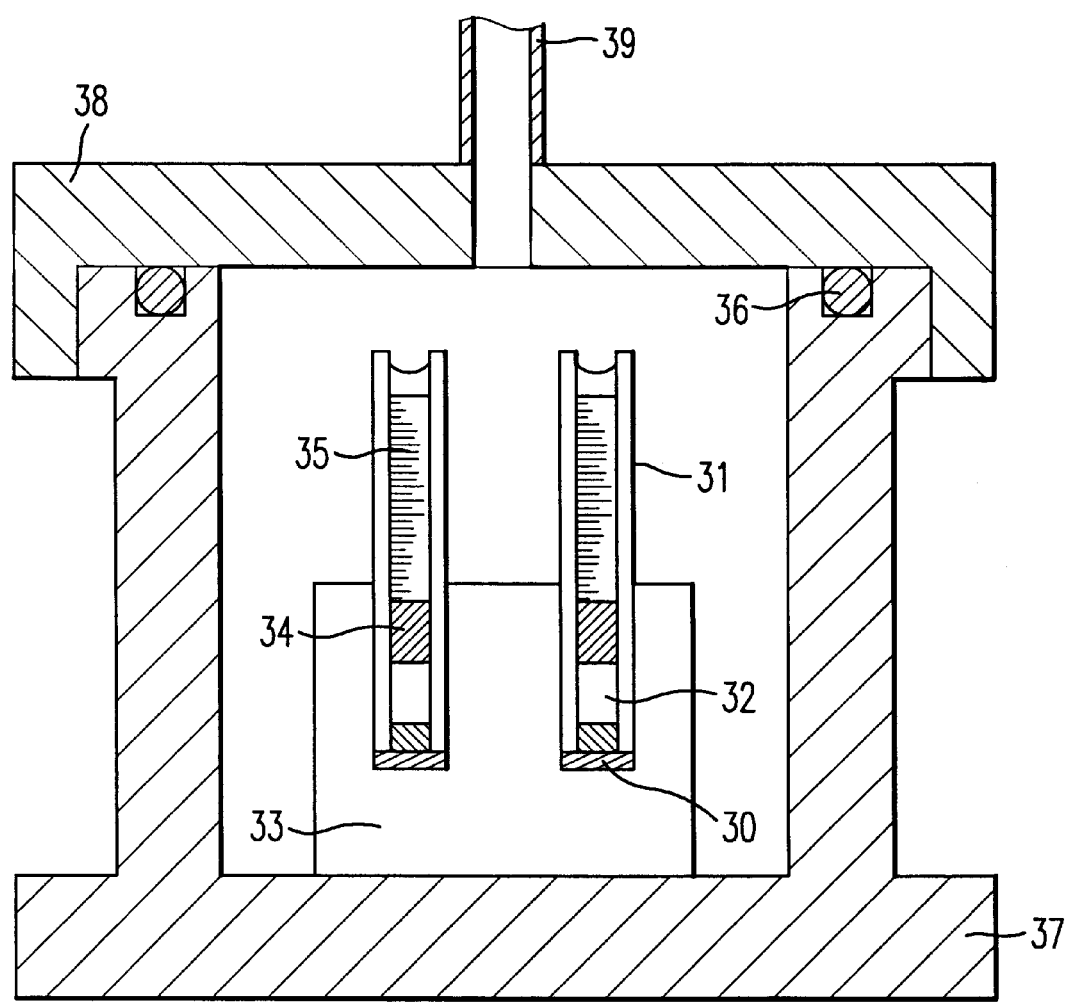

In all the examples described in FIGS. 1 and 2 was used.

The preparation process of the samples to be analyzed and the most detailed equipment used in all the examples are described hereunder still referring to FIGS. 1 and 2.

The equipment and operating process allow the preparation of samples for analysis starting from minimum quantities of matrix in powder form (estimating a precautionary value for the lower limit equal to about 5 mg); these samples are electric conducting and can be analyzed with equipment for inorganic mass spectrometry (or atomic emission spectroscopy) on solids.

An adequate quantity of powder (34) is introduced into the tube (31) made of PTFE closed at one end with a plug

(30) made of tantalum and a spacer (32) made of PTFE; the tube is inserted into an appropriate housing, situated in a brass sample-holder (33). A rod of an appropriate metal ligand (35) is introduced in turn into the tube and brought into contact with the powder.

The sample-holder is housed in the infiltration chamber which, once assembled, is connected to the vacuum line and pressure regulator.

The seal (36) made of Viton is placed on the edge of the container (37), the head (38) is screwed onto the container (37), the infiltration chamber is connected to the two-step pressure reducer (2), the chamber is positioned on the heating plate (4) and the vacuum line (reinforced PVC pipe) (8) is fixed to the T-junction (6), care being taken to close the separation valve (5).

The rotating pump (9) is switched on, waiting until the vacuum, measured by the Pirani (7), is less than $5.0\ 10^{-2}$ mbars.

The valve (5) is slowly opened, controlling that the vacuum is regularly increasing.

When the valve is completely open, the heater (4) is switched on and the temperature regulated to the required value: the ligand melts under a vacuum slightly higher than $10^{-2}$ bars.

When the melting is completed, the cylinder tap (1) is opened, the valve (5) is closed, the communication valve between the compartments of the reducer (2) is opened until 40–50 bars are reached.

The heater is switched off and the chamber is left to cool to room temperature.

After about 20 minutes, the sample-holder (33) is extracted and the samples for analysis are then removed from the PTFE tubes (31).

The samples are removed, after solidification of the ligand, and extracted from the PTFE tube by means of a metal piston, after removing the tantalum plug.

Example 1

40 mg of platinum cement were infiltrated with a cylindrical rod made of In 6N, heating the infiltration chamber for 30 minutes to 200° C. under a vacuum of less than $2.0\ 10^{-2}$ mbars, then pressurizing the chamber with argon (industrial grade) to 40 bars.

The analysis was carried out setting the discharge conditions at 3.0 mA and 1.0 kV: the maximum intensity of the isotope signal $^{196}$Pt is $1.7\ 10^{-10}$ A.

Example 2

20 mg of red phosphorous ($Y_2O_2S$) were infiltrated with a rod made of In 6N, under the same conditions of temperature and pressure described above.

The analysis was carried out setting the discharge conditions at 3.0 mA and 1.0 kV: the signals of the isotopes $^{16}$O, $^{32}$S and $^{89}$Y have maximum intensities of $1.3\ 10^{-12}$ A, $4.1\ 10^{-11}$ A and $1.41\ 10^{-10}$ A, respectively.

Example 3

20 mg of $(NH_4)_2PtCl_6$ were infiltrated with a rod made of Ga 6N5, heating the infiltration chamber for 20 minutes to 60° C. under a vacuum of less than $2.0\ 10^{-2}$ mbars, then pressurizing the chamber with argon to 30 bars.

The analysis was carried out setting the discharge conditions at 2.0 mA and 0.9 kV: the signals of the isotopes $^{14}$N, $^{195}$Pt and $^{35}$Cl have maximum intensities of $2.7\ 10^{-12}$ A, $1.8\ 10^{-13}$ A and $2.1\ 10^{-11}$ A, respectively.

Example 4

80 mg of $GeO_2$ were infiltrated with a cylindrical rod (23 mm in length, 3 mm in diameter) made of In 6N, heating the infiltration chamber for 30 minutes to 200° C. under a vacuum of less than $2.0\ 10^{-2}$ mbars, then pressurizing the chamber with argon (industrial grade) to 50 bars.

The analysis was carried out setting the discharge conditions at 2.5 mA and 1.0 kV: the signals of the isotopes $^{74}$Ge and $^{16}$O have maximum intensities of $1.9\ 10^{-10}$ A, $6.5\ 10^{-12}$ A, respectively.

Example 5

50 mg of GaAs, insulator by doping with Fe, were infiltrated with a rod made of In 6N5, heating the infiltration chamber for 30 minutes to 200° C. under a vacuum of less than $2.0\ 10^{-2}$ mbars, then pressurizing the chamber with argon to 40 bars.

The analysis was carried out setting the discharge conditions at 3.0 mA and 1.0 kV: the signals of the isotopes $^{69}$Ga and $^{75}$As have maximum intensities of $6.0\ 10^{-11}$ A, $1.1\ 10^{-10}$ A, respectively.

Example 6

10 mg of a standard certified lyophilized tissue (NIST RM 8414) were infiltrated with a rod made of In 6N, heating the infiltration chamber for 30 minutes to 200° C. under a vacuum of less than $2.0\ 10^{-2}$ mbars, then pressurizing the chamber with argon to 50 bars.

The analysis was carried out setting the discharge conditions at 3.0 mA and 1.0 kV: the maximum intensity of the isotope signal $^{12}$C is $6.0\ 10^{-11}$ A.

From the data relating to the various matrices, either single or multi-elemental, it is observed that the LoD which can be reached are substantially comparable to those obtained from tests on conventional massive matrices.

Example 7

Dispersion of an Analite in Solution

Increasing aliquots (from 1 to 3.5 microlitres: increase of 0.5 microlitres) taken from standard certified solutions (1 g/L) of various analites (Si, Fe, Cu, Rh, Pd, Pb) were deposited and dried on known quantities (40 mg) of Pt powder, for concentrations ranging form 25 to 87.5 ppm; after homogenization, infiltration was carried out with rods of In 6N and the instrumental results were measured.

For each of the above elements a linear relation is noted between the instrumental result and the concentrations added (linear coefficients higher than 0.98 for seven data pairs).

What is claimed is:

1. Equipment for the preparation of electric conducting composite samples by infiltration in a mould characterized in that it essentially comprises:
   a pressurization/infiltration chamber having at least one opening (39) to connect it by means of appropriate pipes with a vacuum line and a pressure line and devices for sealing both under vacuum and under pressure;
   a sample-holder (33), inside said chamber, made of a material with a high thermal conductivity with one or more seats in each of which a mould is housed consisting of:
   a chemically inert and thermally stable tube (31) made of a non-porous material;
   a plug (30), situated at one end of the tube, of a material which is different from the tube;

a chemically inert and thermally stable spacer (32) of non-porous material, situated inside the tube in contact with the plug;

means for creating a vacuum in the chamber;

means for pressurizing the chamber;

means for the thermal treatment of the sample-holder.

2. The equipment according to claim 1, wherein the tube of the mould is made of plastic.

3. The equipment according to claim 2, wherein the tube of the mould is made of PTFE.

4. The equipment according to claim 1, wherein the plug of the tube is made of tantalum.

5. The equipment according to claim 1, wherein the spacer placed inside the tube is made of plastic.

6. The equipment according to claim 5, wherein the spacer is made of PTFE.

7. A process for the preparation of electric conducting composite samples using an equipment comprising:

a pressurization/infiltration chamber having at least one opening (39) to connect it by means of appropriate pipes with a vacuum line and a pressure line and devices for sealing both under vacuum and under pressure;

a sample-holder (33), inside said chamber, made of a material with a high thermal conductivity with one or more seats in each of which a mould is housed consisting of:

a chemically inert and thermally stable tube (31) made of a non-porous material;

a plug (30), situated at one end of the tube, of a material which is different from the tube;

a chemically inert and thermally stable spacer (32) of non-porous material, situated inside the tube in contact with the plug;

means for creating a vacuum in the chamber;

means for pressurizing the chamber;

means for the thermal treatment of the sample holder;

starting from a powder previously prepared comprising the following steps:

charging a tube with the powder to be analyzed, after inserting the plug and spacer, this operation being effected either before or after the mould has been placed inside the sample-holder;

introduction of a solid ligand into the tube in the area above the powder; closing the pressurization/infiltration chamber after positioning a sealing device;

evacuation from the chamber of the vapor and gases adsorbed on the powder grains bringing the chamber under vacuum;

heating the supporting base of the chamber and consequently both the sample holder and the mould in order to melt the ligand;

pressurization of the chamber up to a pressure of at least 30 bars; extraction of the could from the sample holder, followed or preceded by cooling until the ligand has solidified, removal of the tube plug and extraction from the mould of the composite sample with consequent removal of the spacer.

8. The process according to claim 7, wherein the evacuation is carried out bringing the pressurization/infiltration chamber to a pressure of less than $5.10^{-2}$ mbars.

9. The process according to claim 8, wherein the pressure is equal to or less than $2.10^{-2}$ bars.

10. The process according to claim 7, wherein the pressurization of the pressurization/infiltration chamber is carried out at a pressure ranging from 40 to 50 bars.

11. The process of claim 7, wherein the tube of the mould is made of plastic.

12. The process of claim 11, wherein the tube of the mould is made of PTFE.

13. The process of claim 7, wherein the plug of the tube is made of tantalum.

14. The process of claim 7, wherein the spacer placed inside the tube is made of plastic.

15. The process of claim 14, wherein the spacer is made of PTFE.

* * * * *